(12) United States Patent
Knott et al.

(10) Patent No.: US 8,595,913 B2
(45) Date of Patent: Dec. 3, 2013

(54) STENT CRIMPING METHODS

(75) Inventors: Boyd V. Knott, Menifee, CA (US); Samit Kadakia, Corona, CA (US); Leopoldo Ortega, Murrieta, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 407 days.

(21) Appl. No.: 12/895,646

(22) Filed: Sep. 30, 2010

(65) Prior Publication Data

US 2012/0079706 A1  Apr. 5, 2012

(51) Int. Cl.
*B23P 11/00* (2006.01)

(52) U.S. Cl.
USPC ................................ 29/516; 29/280; 606/108

(58) Field of Classification Search
USPC ............ 29/235, 447, 508, 516, 517; 606/108, 606/194
See application file for complete search history.

(56) References Cited

U.S. PATENT DOCUMENTS

| | | | |
|---|---|---|---|
| 5,992,000 A * | 11/1999 | Humphrey et al. ............. | 29/516 |
| 6,179,867 B1 * | 1/2001 | Cox ............................. | 623/1.15 |
| 6,312,459 B1 * | 11/2001 | Huang et al. ................. | 623/1.15 |
| 7,156,869 B1 * | 1/2007 | Pacetti .......................... | 623/1.11 |
| 7,648,727 B2 * | 1/2010 | Hossainy et al. ............. | 427/2.25 |
| 7,763,198 B2 * | 7/2010 | Knott et al. ................... | 264/249 |
| 2004/0181236 A1 | 9/2004 | Eidenschink | |
| 2005/0183259 A1 * | 8/2005 | Eidenschink et al. .......... | 29/508 |
| 2006/0123874 A1 * | 6/2006 | Motsenbocker ............... | 72/402 |
| 2009/0088829 A1 * | 4/2009 | Wang et al. .................... | 623/1.11 |
| 2009/0282669 A1 * | 11/2009 | Von Oepen et al. ............ | 29/447 |
| 2010/0115755 A1 * | 5/2010 | Pacetti ............................ | 29/446 |

FOREIGN PATENT DOCUMENTS

WO  WO 2005/053937  6/2005

OTHER PUBLICATIONS

U.S. Appl. No. 11/938,127, filed Nov. 9, 2007, Wang.
International Search Report for PCT/US2011/051242, mailed Dec. 6, 2011, 4 pgs.

* cited by examiner

*Primary Examiner* — Minh Trinh
(74) *Attorney, Agent, or Firm* — Squire Sander (US) LLP

(57) ABSTRACT

A process for crimping stents includes a multi-stage process producing a desired stent retention and crimped profile in a reduced amount of time. The process achieves results by utilizing particular combinations of heat and pressure during the crimping process, which was found to produce the desired results.

12 Claims, 1 Drawing Sheet

STENT CRIMPING METHODS

BACKGROUND OF THE INVENTION

1. Field of the Invention

The present invention relates to drug-eluting medical devices; more particularly, this invention relates to processes for crimping a stent to a delivery balloon.

2. Background of the Invention

A known stent retention process consists of three operations, stent crimp, split mold and stent press. Stent crimp is the process by which the stent is placed on the catheter. First the stent is placed on a pre-crimp mandrel and placed in the crimp machine. The crimp machine closes onto the stent applying radial force causing the scent's diameter to be reduced to that of the pre-crimp mandrel. The pre-crimp mandrel diameter is selected based on the delivery systems folded balloon profile. After pre-crimp, the stent is removed from the mandrel and placed on a balloon delivery system, balloon catheter, or delivery system. The balloon catheter is placed into the crimp machine and radial force applied to reduce the diameter of the stent onto the balloon catheter. No heat or catheter inflation pressure is applied during this operation.

The delivery system now with the stent in place on the balloon is sent to the split mold operation. The split mold operation applies heat and pressurizes the delivery system for a specified amount of time to a specified increased diameter causing the balloon to "pillow" between the stent struts, which further increases mechanical interaction between balloon and stent. The delivery system is then moved to a stent press where the stent and balloon are placed into a press machine and radial force again applied to reduce the profile to a specified diameter, thereby again increasing the mechanical interaction between balloon and stent.

Related devices are mentioned in U.S. Pat. No. 7,763,198 ('198 patent) which is commonly owned with the present application. An example of the "split mold" is depicted in FIGS. 1-3 of the '198 patent. The bore of the split mold is machined within the block that forms the body of the mold, with the two halves of the mold in place together during the machining. The diameter of the mold bore (FIG. 12) may be slightly larger than the outer diameter of a crimped stent on the balloon of eth balloon catheter, or matched to that diameter, so that the stent does not radially expand during the stent mounting. The balloon is heated by heating the mold with via a conductive heating element member in the form of metal platens.

With the balloon catheter in position within the bore of the split mold, the mold is heated to an elevated temperature sufficient to soften the balloon but lower than the thermal limit of the drug disposed on or in the stent. The mold is heated to a temperature of about 160° F. to about 190° F., with the balloon catheter therein during the stent mounting procedure, to soften a balloon formed of polymeric material. The '198 patent shows a transverse cross section of the balloon catheter with stent gaps partially filled by balloon material so that the balloon material contacts and partially encapsulates the side surfaces of the stent struts, to mount the stent on the balloon.

According to the '198 patent, during the initial, or pre-crimping and/or re-crimping process, i.e., before and after, respectively, the split-mold process the balloon may be pressurized and heated to increase the protrusion of balloon material into the openings in the stent pattern, thereby further increasing stent retention on the balloon. The balloon may be pressurized in the range of 10 to 300 pounds per square inch (psi). The balloon may be heated to the range of about 70 degrees to 250 degrees Fahrenheit (21 to 121 degrees Celsius) during re-crimping. The mounted stent can be heated to about 130 degrees Fahrenheit (54 degrees Celsius) during re-crimping. The balloon may be pressurized to about 70 psi.

The '198 patent discloses various combinations of crimping, balloon pressure and heating of stent and balloon to reduce the stent profile and increase the retention of stent to balloon. However, the pre-crimp, split-mold and re-crimp phases of the process are performed separately using separate machines. This process is time-consuming and does not yield an optimal combination of profile and dislodgment or retention force of the balloon and stent. Dislodgment or retention force means the force needed to pull or dislodge the stent from the balloon. Further details on the meaning of dislodgment force or stent retention force may be found in U.S. application Ser. No. 11/938,127. What is needed is a process that simplifies the process of crimping a stent to a balloon, while also achieving the desired crimped stent profile and increasing the dislodgment force. Accordingly, there is a continuing need to improve upon the crimping methods for stents.

SUMMARY OF THE INVENTION

The invention provides a process and apparatus for crimping a stent to a balloon that reduces the processing time, involves fewer steps and produces an increased dislodgment force for a stent crimped to a balloon. Prior processes for crimping a stent to a balloon have involved a pre-crimp process, followed by a balloon pressurization step within a mold. This step was then followed by a final crimp stage where the stent is crimped to a final diameter. This process is time consuming and requires the use of multiple machines for performing the process. Moreover, the dislodgment force was in need of improvement to facilitate better retention of the stent on the balloon during delivery to a target site in a vessel.

It was discovered, unexpectedly, that when parameters of the crimping process are varied in a particular manner, the same retention and target outer diameter profile for the catheter could be achieved without reducing yield, i.e., no increased rate of stent or balloon damage for a batch run using the new process and dislodgment force may be increased without introducing other undesired qualities. In tests conducted using the new process the processing time could be reduced by about 70%, without reducing yield and with increased dislodgment force for the crimped stent and balloon.

Accordingly, the advantages of the process according to the invention may be described as two-fold: a significant reduction in the duration of a crimping process, primarily by a reduction in the dwell time during pre-crimp, encapsulation, and final crimp; and increased dislodgment force without effecting the stent profile or deliverability of the stent through a tortuous pathway.

The process may be described as having three stages, which may proceed in a more or less continuous manner. Stage 1 is a pre-crimp stage. The stent is loaded onto a mandrel and placed in a crimping machine where an iris type mechanism closes crimping jaws or blades onto the stent and reduces the profile of the stent down to a specified dimension. In Stage 2, the stent is loaded onto the balloon catheter delivery system and placed back into the crimping machine where the iris type mechanism closes down to a specified dimension, the catheter is pressurized and the distal end of the delivery system is heated for a specific amount of time to cause pillowing of the balloon between stent struts. In Stage 3, the iris type mechanism may then open and closes to specified dimensions to decreasing the stent dimension or profile, which causes increased mechanical interaction between balloon and stent. Opening and closing the iris type mechanism onto the stent several times may be performed in order to work the stent material, to reduce recoil, decrease system profile and further increase the mechanical interaction between balloon and stent.

In an alternate embodiment of Stage 3, the iris-type mechanism does not increase in diameter. Rather, the iris-type mechanism closes from the Stage 2 iris diameter to a smaller, Stage 3 diameter. This Stage 3 diameter may be less than the final crimp diameter. Catheter pressurization may also be added to Stage 3 processing to help retain/increase the pillowing at the smaller dimension, thereby further increasing the mechanical interaction between balloon and stent. Adding catheter pressurization prior to or during the iris type mechanism reaching the final specified dimension or profile may also increase the mechanical interaction between balloon and stent above just pressurizing the system at the specified dimension for the specified dwell time. By pressurizing during the closing of the iris, for example, the stent and balloon position is fixed or constrained relative to each other, which allows for an existing imprint of the stent on the balloon (formed during stage 2) to be substantially retained or unaltered when the stent is reduced in diameter, which increases the mechanical interaction.

The setting ranges for a crimping process may include a temperature of 110° F.-250° F. The upper range for temperature may be defined in terms of the material characteristics of the coating material. For example, if a drug-polymer coating is particularly sensitive to temperature increases the upper temperature range may be limited by the drug-polymer coating. Alternatively, the lower range of this temperature, may, according to some embodiments, be defined by the lower limit of the glass transition temperature for the balloon material, the lower glass transition temperature for the co-block polymer PEBAX. It is also believed that the temperature may, in some embodiments, be reduced to about room temperature if the balloon pressure is high enough during the crimping process.

Dwell times at a processing stage may range between about 1 sec. to 90 sec., a crimped diameter for the stent ranging from about 0.018" to 0.400" and catheter pressurization during Stages 1-3 being between 50 psi and 400 psi. The number of Stage 3 iterations may range from 1 to 8, in which each cycle includes a diameter reduction, balloon pressurization and dwell time to increase stent retention and arrive at the desired final crimp diameter. In other embodiments the number of Stage 3 iterations may be higher than 8, e.g., to work material to reduce recoil and/or increase the dislodgment force further. In a preferred embodiment the process parameters are Temperature: 170° F.;
Stage 1, 2 and 3 dwell times: 1 seconds, 30 seconds, and 3 seconds, respectively;
Stent diameters at the conclusion of Stages 1, 2 and 3 are, respectively, 0.0336", 0.052", and 0.040";
Maximum catheter pressurization at each stage: 300 psi; and
Number of Stage 3 iterations: 1 to 6

In accordance with the foregoing objectives, the invention provides, in one embodiment a method for crimping a stent to a balloon including the steps of i. elevating the temperature of the stent; ii. pre-crimping the stent including reducing the stent diameter to a first diameter, wherein the stent has a first elevated temperature while the diameter is being reduced to the first diameter; iii. removing the stent from the crimp head following the pre-crimping step and placing the stent on a balloon catheter to assemble a stent-catheter assembly, a balloon of the balloon catheter capable of being pressurized through a proximal end of an inflation lumen of the balloon catheter; iv. placing the stent-catheter assembly within the crimp head and increasing the stent temperature to a second elevated temperature, while the stent has the second elevated temperature, pressurizing the balloon via the inflation lumen while the stent-catheter assembly is within the crimp head; following step iv, pressing the stent into the balloon, the stent having a third elevated temperature, step v including reducing the stent diameter using the crimp head from about the second diameter to about the final crimp diameter while maintaining the balloon pressure; and removing the stent-catheter assembly from the crimp head.

In some embodiment, prior to removal of the stent-catheter assembly from the crimp head a leak test may be performed on the stent-catheter to check for any leaks or damage to the balloon. A leak test raises balloon pressure to a specified amount, e.g., 150 psi, then monitors balloon pressure to see whether the pressure changes over a specified dwell period, e.g., 1-2 minutes. In other embodiments the leak test may be performed outside of the crimp head, such as when it is desirable to have the leak test performed at body or room temperature (for batch processes with the crimp blades at an elevated temperature it may be preferable, therefore, to have the leak test done outside the crimp head so that a constant crimp head temperature can be maintained throughout the batch process).

Step iv may include placing a sheath having an inner diameter of about 25% greater than the stent first diameter over the stent to protect a coating on the stent, wherein the sheath has a radial stiffness such that the presence of the sheath over the stent provides the up to about 25-30% of the first diameter restraint on stent expansion during step iv. This range may be increased and the sheath may be further aided by the crimper blades to provide a restraint on stent expansion to facilitate the interlocking of balloon material with stent struts.

The pressing the stent into balloon step (step v) may include having the stent reduced by up to about 40% in diameter while simultaneously having the stent maintain an elevated temperature and balloon pressure being applied, e.g., about 150-300 psi. In a preferred embodiment pressure and temperature is maintained from the prior art during the up to 40% diameter reduction. It has been found that there is a significant increase in dislodgment force, far more than would have been expected, when pressure and temperature are maintained during this diameter reduction. In one embodiment the up to 40% reduction moves the stent diameter to less than the final crimp diameter followed by a three second dwell. Additionally, the stent and balloon are then further cycled including repeatedly applying then withdrawing the crimp head and adjusting balloon pressure to further increase dislodgment force.

According to another embodiment, a method for crimping a stent to a balloon includes the steps of i. elevating the temperature of the stent; ii. pre-crimping the stent including reducing the stent diameter from a first diameter to about a final, crimped diameter while the stent is supported on a mandrel within a crimp head, wherein the stent temperature has the elevated temperature while the diameter is being reduced to about the final crimped diameter; iii. removing the stent and mandrel from the crimp head following the pre-crimping step and placing the stent on a balloon catheter to assemble a stent-catheter assembly, a balloon of the balloon catheter capable of being pressurized through a proximal end of an inflation lumen of the balloon catheter; vi. placing a protective sheath over the stent, the protective sheath having a radial stiffness and an inner diameter that is about 20-30% greater than the stent outer diameter after step ii; v. placing the stent-catheter assembly within the crimp head and increasing the stent temperature to the elevated temperature; vi. while the stent has the elevated temperature, coupling the stent to the balloon including the steps of (a) pressurizing the balloon via the inflation lumen while the stent-catheter assembly is within the crimp head, wherein the balloon pressure is maintained at a maximum pressure for a predetermined time period and the stent is restrained from expanding beyond about 20-30% of its diameter by the protective sheath, and (b) following step (a), while maintaining the elevated temperature and balloon pressure reducing the diameter of the stent to a third diameter, less than about the final crimped diameter using the crimp head; and vii. removing the stent-catheter assembly from the crimp head.

Incorporation by Reference

All publications and patent applications mentioned in this specification are herein incorporated by reference to the same extent as if each individual publication or patent application was specifically and individually indicated to be incorporated by reference, and as if each said individual publication or patent application was fully set forth, including any figures, herein.

DETAILED DESCRIPTION OF EMBODIMENTS

For purposes of this disclosure, a "stent" means an open-walled tubular body of interconnected, spaced-apart struts with gaps between adjacent stent struts. The struts may form rings having a serpentine wave pattern of opposed turns and which are longitudinally spaced apart and connected by links. The stent, when crimped to a balloon undergoes a process of plastic deformation from a starting or manufactured diameter to a final or crimped diameter. The stent is expanded to a deployed diameter by being plastically deformed by expansion of the balloon.

A stent having a pattern as described in U.S. Pat. Nos. 6,312,459 or 179,867 may have a starting, or manufactured outer surface diameter of 0.07 in. The stent is made from a metal or metal alloy. The stent may be crimped to a non-compliant balloon made from PEBAX material. When deployed the stent has a nominal 3 mm (0.118 in) outer diameter and 18 mm (0.708 in) length. For purposes of this disclosure, this stent will be referred to as the 3018 stent, or "the stent", however, it will be appreciated that the principles discussed are not limited to only this stent or stents of this size or design. The target final crimped diameter for the stent is about 0.04 in. During the entire process—initial crimp, balloon inflation, final crimp and leak test—the stent is contained within a TEFLON or other suitable polymeric sheath, which protects the surface of the stent, particularly the drug-polymer coating from damage when coming into contact with metal crimper blades. For a 3.00 mm deployed diameter stent, e.g., the 3018 stent, and 0.04 in crimped diameter a sheath is preferably chosen having an inner diameter of about 0.052 in. Following the leak test the sheath may be peeled away from the outer surface of the stent.

Figure 1A:
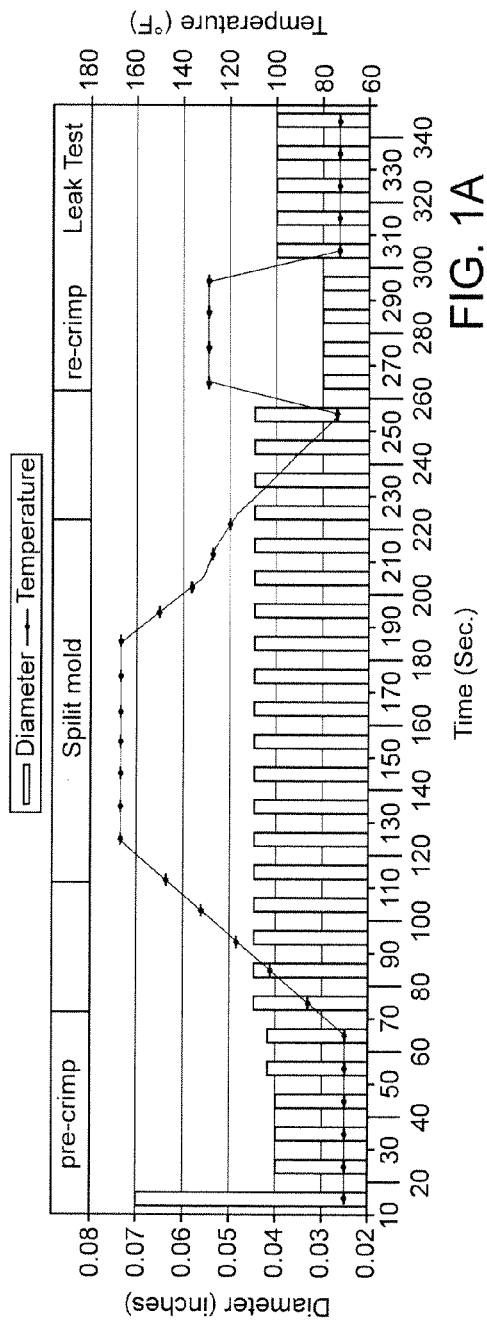
FIG. 1A is a plot showing temperature and stent outer diameter verses time for a prior art process. This process may be practiced in accordance with the principles outlined in U.S. Pat. No. 7,763,198.

FIG. 1A shows processing time verses temperature and pressure values for a prior art crimping process similar to a process described in U.S. Pat. No. 7,763,198. In stage 1 of this process, the stent is placed within a crimper head having a temperature of about 70 degrees Fahrenheit and the diameter is reduced down to about 0.04 in. following a dwell period of about 1 minute the stent is removed from the crimper and placed on a balloon of a balloon catheter then re-inserted into the split mold device described in U.S. Pat. No. 7,763,198. The temperature is raised to a maximum of about 170 degrees Fahrenheit and pressure is raised while the stent is held within the split mold, which restrains outer diameter movement of the stent to about 0.048 in. After a period of about 185 seconds within the split mold the stent and balloon are removed from the split mold then placed back within a crimper for a re-crimp of the stent to the balloon. During this re-crimp period the stent is raised to a temperature of about 130 degrees Fahrenheit and the crimper's iris moved to 0.03 in, which reduces the stent diameter to about 0.03 in. After an additional dwell of about 40 seconds at 130 degrees Fahrenheit the crimped stent and balloon are removed from the crimper and a leak test performed. The leak test checks for any damage to the balloon. A leak test maintains the stent diameter at about the 0.04 in profile while the balloon pressure is inflated, e.g., to about 300 psi, and held at that pressure for about 60 seconds. The balloon pressure is monitored during this 60 second period to determine whether there is any pressure drop (indicating possible balloon damage).

The process just described is time consuming. Additionally, it is desirable to increase the dislodgment force beyond that which is possible when using the process according to FIG. 1A. For these and other reasons, which become apparent from the discussion that follows, the inventors were able to improve upon the process summarized above. It was discovered, unexpectedly that during the course of reducing the length time needed for the crimping process, not only was there a significant reduction in processing time, but it was also found that the stent dislodgment force could be increased significantly when utilizing the processes according to the disclosure.

Figure 1B:
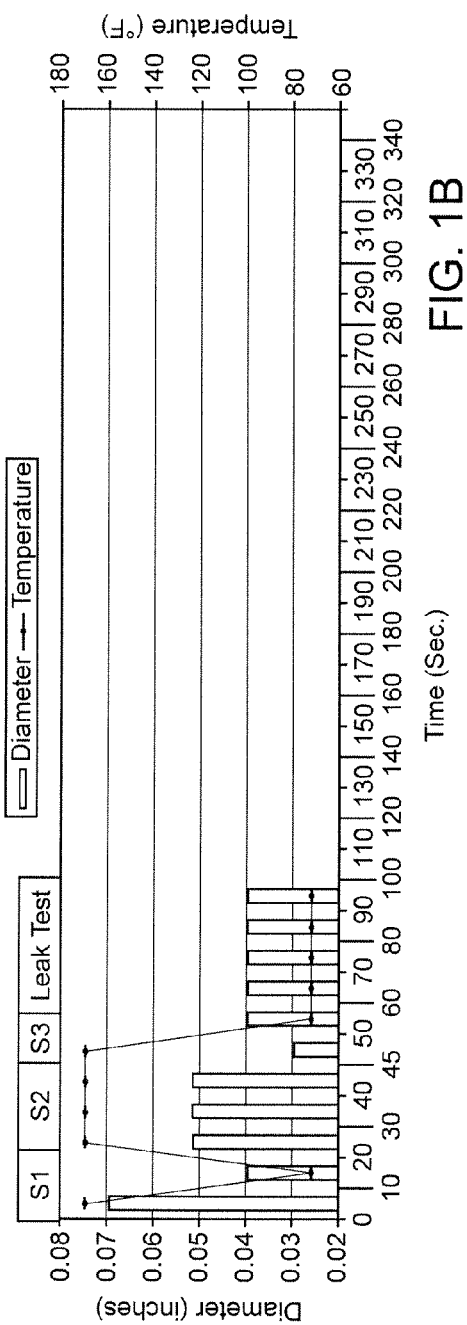
FIG. 1B is a plot showing a process according to the disclosure. As can be readily discerned from a comparison between FIGS. 1A and 1B, the processing time for arriving at the final crimp diameter and desired dislodgment force is reduced by about 70%.

The following discussion describes a process summarized in FIG. 1B. As can be readily appreciated from FIG. 1B the processing time has been reduced from about 350 seconds to about 90 seconds. According to one embodiment of a process corresponding to FIG. 1B, all stages of the crimp process are performed using a single crimper device. The process of FIG. 1A has been performed using up to three devices: a first crimping device (pre-crimp), the split mold and a second crimping device (re-crimp). Notably, the dwell times have been reduced significantly. Additionally, the process seeks to maintain about a 170 degree Fahrenheit temperature for each stage, which is preferable as it obviates the need to constantly adjust the temperature settings between each stage (as in the case of FIG. 1A). Also, by utilizing a single crimping head, it becomes possible to transition from the second stage ("S2") to the third stage ("S3") while maintaining a desired temperature and/or balloon pressure. This later ability, it was found, can yield increased dislodgment force. In one example, the stent dislodgment force using the process of FIG. 1A was about 2.2 lbs, whereas the dislodgment force was about 2.5 lbs when using processes associated with FIG. 1B for the same stent final and starting diameter and balloon properties.

In other examples the dislodgment force was found to increase by about 12% when processes associated with FIG. 1B were used.

The stent at 0.07 in outer surface diameter is placed on a 0.0336 in outer surface mandrel defining an initial crimped diameter for the stent. The stent-mandrel assembly are centered in an iris-type crimp head and the stent outer surface diameter reduced down from 0.07 in to about 0.04 in. The diameter reduction from 0.07 in to 0.04 in occurs over a period of about 10 seconds, or the blades of the crimper translate from the iris diameter of 0.07 in to an iris diameter of 0.04 in at a rate of 0.3 in/sec. There is a 5 second dwell period before the iris is withdrawn from the stent surface. In another embodiment the rate of diameter reduction is about 0.05 in/sec to the 0.04 in outer diameter, followed by a 5 second dwell time.

The stent, when initially at the 0.07 in outer surface diameter and within the crimper head has an average temperature of about 170 degrees Fahrenheit. Over the second period for diameter reduction to 0.04 in outer surface diameter and dwell, the stent temperature is reduced, e.g., the heat source is discontinued once the diameter reduction begins. The temperature is reduced when the stent is removed from the crimper head (as discussed below). The stent average temperature reaches about 70 degrees Fahrenheit. The temperature drop plotted in FIG. 1B after about 5 and 15 seconds reflects, therefore, the temperature drop of the stent after it is removed from the 170 degree heated crimper head. Preferably, the crimper head is maintained at about 170 degrees for steps S1, S2 and S3.

The heat transfer mechanism used to arrive at the 170 degree starting temperature may be heated crimper blades to about this temperature, heated gas, a heated supporting metal mandrel supporting the stent within the crimp head, or a combination of the above. In a preferred embodiment the temperature is raised by only heating the blades of the crimper. Thus, the stent temperature is raised to about 170 degrees Fahrenheit by only the convected and radiated heat from the blades forming the crimper iris.

After the stent diameter has been reduced to about 0.04 in the crimper jaws during stage S1, the stent is withdrawn from the heated crimper head. The stent is then removed from the mandrel and placed on the delivery system, i.e., a non-compliant, folded PEBAX balloon of a balloon catheter. The stent is aligned between balloon markers then placed back into the crimper head for the next stage (S2) of the crimping process. A sheath is then placed over the stent to protect a polymer-drug coating on the stent from possible damage that might occur when the blades of the crimper come into contact with the stent. The sheath size may be selected according to an inner diameter size defining the maximum extent the stent will expand during stage S2 when the balloon pressure is increased. In a preferred embodiment, a TEFLON sheath having an inner diameter of about 0.052 in is used for the stent having the initial crimp diameter of about 0.042 in prior to S2.

The selection of the inner diameter of the protective sheath is believed to have an effect on the amount of desirable pillowing of the balloon between stent struts during S2. If the sheath diameter is too small, it is believed that less than a desirable amount of pillowing will occur as the balloon is restrained from expanding; thereby preventing the balloon material from extending between stent struts. If the sheath diameter is too large, then the stent can expand too much or other problems can occur during the subsequent stage S3. Either or both of displacement or shifting of the stent relative to the balloon occurs, i.e., shifting the stent's alignment with respect to the balloon markers, or there is less pillowing of balloon material between struts since the balloon and stent can more freely move outward relative to each other, rather than forcing balloon material between stent struts due to a radial restraint imposed by the inner sheath diameter. A protective sheath diameter should also not be made too large as this may cause the sheath to crumple or fold over itself rather than be compressed during the final crimp (S3). It is believed that, to produce the desirable results for a stent with the 3018 stent dimensions, for example, the sheath inner diameter was selected to be between about 0.046 to 0.056 in, or more narrowly between about 0.0048 to 0.054 in for an initial crimp stent diameter of about 0.042 in. In other embodiments the sheath inner diameter may be chosen to be between about 15-30%, 20-30%, or 20-25% greater than an outer diameter of a polymer-drug coated stent. Depending on the diameter of the balloon being processed, a range from about 0.038" to about 0.080" is contemplated. For example, in the case of the 3018 stent the range may be between about 0.042" to 0.065".

The catheter's luer fitting is connected to a pressure source for supplying inflation pressure to the balloon lumen while the stent-catheter assembly is disposed within the crimper head. Balloon pressure is used in combination with other parameters such as heat and temperature during Stages S2 and S3 of the crimping process of FIG. 1B to arrive at a desired retention force and outer profile.

For stage S2 the stent, aligned on the balloon, has a diameter of about 0.04 in. or slightly higher (e.g., about 0.042 in) due to elastic recoil of the material when the crimper jaws or blades are withdrawn. The stent-balloon assembly (stent and balloon within a protective sheath) is placed back into the heated crimper. After a period of about 5-10 seconds the stent again attains a temperature of about 170 degrees. Concurrently with the rise in temperature, pressure is supplied to the balloon lumen, which causes the balloon diameter and stent outer surface diameter to increase according to the sheath size (as discussed earlier). In one example, the inflation causes the stent outer surface diameter to increase from about 0.042 in to about 0.052 in. In other embodiments the stent outer surface may be capable of increasing 25-40%, 25-35%, or more narrowly 28-32% when the balloon is pressurized. The balloon pressure may be increased to a peak pressure of about 300 psi during this phase of the crimping process. In other embodiments, balloon pressure may be 150 psi or between 150-300 psi, which pressure may be selected based on the length of time for S2, e.g., for a lower pressure the dwell period may be increased.

In another embodiment, pillowing may be controlled or enhanced by using the crimper jaws, rather than, or in addition to a selected sheath inner diameter for enhancing pillowing. By selecting a sheath inner diameter of about, e.g., 0.052 in for the 3018 stent, and in addition (or alternatively) setting the crimper jaws at a limit compressive force (beyond which the blades deflect away), or fixed diameter or enforced displacement setting, the pillowing effect between stent and balloon may be affected to improve results. In one embodiment, the crimper blades are set to a low compressive force, in addition to the sheath being present to improve thermal conductivity from the blades to the stent. By disposing blades to contact the sheath the stent temperature may be more quickly raised than the case where the blades are offset from the sheath. In another embodiment the crimper blades may be withdrawn at a rate matching the approximate rate (or slightly slower) of diameter increase of stent diameter without the blades applying a radial compressive force.

The crimper blades may be set in position to form an iris diameter of about, or slightly larger than the sheath outer diameter, respectively, so that the stent outer surface diameter cannot exceed this diameter even when the sheath is stretched (for thin-walled sheaths) during balloon expansion. Alternatively, the crimper blades may be programmed to apply a slight compressive force to the stent and sheath that is exceeded by the forces of the stent on the blades as the stent is expanded by balloon pressure. By applying this additional compressive load (beyond that imposed by the sheath on the stent, balloon pillowing may be further enhanced. In some embodiments a limit of 0.052 in maximum outer surface diameter reached by the stent may be achieved by either imposing an enforced maximum displacement (fixed displacement) by fixing the iris at about the sheath outer diameter or slightly larger, or a fixed force imposed by the crimper, which is overcome by balloon pressure over the S2 period so that at the end of the pressurization period the stent diameter is at about 0.052 in.

In a preferred embodiment, a sheath having an inner diameter of about 0.052 in for an about 0.042 in crimped stent profile is used to restrain outward movement during stage S2. During S2 the stent outer diameter increases from about 0.042 in about 0.052 in or to a diameter about equal to the sheath inner diameter. According to the disclosure, during S2 the stent outer diameter may be increased by about 15-30% or more narrowly about 20-25% and still more narrowly to about 22-24% during S2 to achieve a desired amount of pillowing before transitioning to stage S3. The duration of S2 may be about 30 seconds for these ranges of diameter increase at a temperature of 170 degrees and pressure of about 300 psi.

As mentioned above, stage S2, the balloon pressurization period, is intended for increasing or encouraging a pillowing effect between stent and balloon. "Pillowing effect" means the balloon material extending between and through gaps in stent struts as balloon pressure is increased under a restraint, i.e., a protective sheath inner diameter sized according to the stent outer diameter. Pillowing facilitates the interlocking of balloon material with stent struts. The temperature is about 170 degrees Fahrenheit, which can facilitate the pillowing effect as the balloon material, being expanded by the lumen pressure and its surface and stent surface having a raised temperature, can better extend between the stent struts. Once located between stent struts, the stent dislodgment force is increased significantly over a stent that relies only on friction between the crimped stent and balloon. Preferably, the balloon used does not contain ridges or protrusions to facilitate stent retention. Rather, results were achieved with a PEBAX balloon having a relatively smooth surface.

The stent and balloon are kept within the crimper head as the process transitions from Stage S2 to Stage S3 in FIG. 1B. During Stage S3 the stent diameter is reduced down to about the 0.04 in diameter again. A balloon pressure, e.g., 300 psi, and temperature of 170 degrees Fahrenheit are maintained during the diameter reduction from about the 0.052 in following Stage 2, and/or during the dwell period of about 3 seconds for S3. For S3 there may be successive crimp, dwell and release intervals for purposes of working metal to reduce recoil when the jaws are removed. Additionally, it was found that this cycling between crimp diameters (e.g., applying then releasing crimp jaws) also increased the dislodgment force. In one embodiment there are 7 periods where the stent is reduced in diameter, a dwell period follows, then a brief period where the jaws are released or moved to a larger diameter, e.g., from 0.03 in to 0.03 in. For S3 the crimp diameter may be enforced to a reduced diameter by the crimper blades, then allowed to recoil to up to a final crimp diameter.

Tables 1, 2 and 3 below provide the parameters for stent crimping for some of the embodiments discussed above. The target outer diameter for the final crimped size was 0.04 in for the 3018 stent in Tables 1, 2 and 3 following the leak test. After the leak test the protective sheath is removed.

Under column "Speed (in/sec)" the values of 0.05 in/sec and 0.300 in/sec are given. In some embodiments the rate at which the crimper blades are brought down on the stent to decrease its diameter, or rate at which the balloon is inflated can be altered to affect the amount of stent retention to the balloon. In the embodiments the rate of balloon expansion, and/or crimping rate may be between 0.05 and 0.300 in/sec.

Examples 1 and 2, summarized under Tables 1 and 2, respectively, are the same, except that in Example 1 balloon pressure is applied only during the dwell periods of S3. The crimp head speed is 0.05 in/sec for Example 1 and 0.300 in/sec for Example 2. Balloon pressure is applied during the diameter reduction and dwell periods of S3 in Example 2. Pressure was applied during all traverse times including from 51 to S2 in addition from s2 to s3 for Example 2 (as well as Examples 3 and 4, below). In other embodiments, it is contemplated that results may be improved further by applying balloon pressure (constant or varying) during all traverse times, including during each step of a multi-stage S3 process (e.g., Examples 3 and 4). The resulting dislodgment force was greater for Example 2 (1.0 lbs compared with 1.4 lbs, or about 40% increase, over Example 1).

TABLE 1

Example 1 crimping parameters (3 × 18 metal stent)

| Stage | Diameter (in) | Speed (in/sec) | Dwell (sec) | Balloon Pressure (psi) | mandrel size (in) | Temp (deg. F.) | |
|---|---|---|---|---|---|---|---|
| S1 | .0336 | .05 | 5 | 0 | .036 | 170 | pressurize balloon during dwell only |
| S2 | .070 | .05 | 30 | 300 | | | |
| S3 | .040 | .05 | 3 | 300 | | | |

TABLE 2

Example 2 crimping parameters (3 × 18 metal stent)

| Stage | Diameter (in) | Speed (in/sec) | Dwell (sec) | Balloon Pressure (psi) | mandrel size (in) | Temp (deg. F.) | |
|---|---|---|---|---|---|---|---|
| S1 | .0336 | .300 | 5 | 0 | .036 | 170 | pressurize balloon during dwell and diameter reduction |
| S2 | .070 | .300 | 30 | 300 | | | |
| S3 | .040 | .300 | 3 | 300 | | | |

Examples 1 and 2 were compared to a crimping process in which no balloon pressure was applied during Stage 3. It was found that the dislodgment force increased by about 0.4 lb when balloon pressure was present during Stage 3. The final outer diameter increased by about 0.003 mm when balloon pressure was applied during Stage 3.

Example 3 shows multiple final crimp cycles applied during stage S3. In this example, several cycles of crimp, dwell and release under balloon pressure were applied. The period where the crimp blades are withdrawn are indicated by the diameter 0.3 in. As shown, following a 3 second dwell the crimp head force is relieved and 300 psi reduced to about 0 psi for about 0.1 second (essentially, the pressure is relieved and head withdrawn for only a very brief period), then the crimp head applied again and balloon pressure of 300 psi re-applied. After the initial diameter reduction to 0.04 mm, the same process of crimp, dwell and release are applied to the 3018 stent, as shown.

TABLE 3

Example 3 crimping parameters (3 × 18 stent)

| Stage | Diameter (in) | Speed (in/sec) | Dwell (sec) | Balloon Pressure (psi) | mandrel size (in) | Temp (deg. F.) |
|---|---|---|---|---|---|---|
| S1 | 0.0336 | 0.100 | 5 | 0 | .036 | 170 |
| S2 | 0.070 | 0.100 | 30 | 300 | | |
| S3 | 0.040 | 0.300 | 3 | 300 | | |
| S3 | 0.300 | 0.100 | 0.1 | 0 | | |
| S3 | 0.040 | 0.300 | 3 | 300 | | |
| S3 | 0.300 | 0.100 | 0.1 | 0 | | |
| S3 | 0.040 | 0.300 | 3 | 300 | | |
| S3 | 0.300 | 0.100 | 0.1 | 0 | | |

The Example 1 crimping process was compared to the Example 3 crimping process. It was found that when the crimping process of Example 3 is used, the crimp profile may be reduced to about 0.0388 in verses about 0.0398 and the dislodgment force increased over the Example 1 process. Thus, using the Example 3 process about the same final crimp diameter, or slightly less, was achieved while, at the same time, the dislodgment force was increased.

In Example 4, the crimp head is not opened and closed as in Example 3 but instead, moved between a 0.04 in iris diameter to 0.03 in iris diameter. This additional example is summarized in TABLE 4, below.

TABLE 4

Example 4 crimping parameters (3 × 18 stent)

| Stage | Diameter (in) | Speed (in/sec) | Dwell (sec) | Balloon Pressure (psi) | mandrel size (in) | Temp (deg. F.) |
|---|---|---|---|---|---|---|
| S1 | 0.0336 | 0.100 | 5 | 0 | .036 | 170 |
| S2 | 0.070 | 0.100 | 30 | 300 | | |
| S3 | 0.030 | 0.300 | 3 | 300 | | |
| S3 | 0.040 | 0.100 | 0.1 | 0 | | |
| S3 | 0.030 | 0.300 | 3 | 300 | | |
| S3 | 0.040 | 0.100 | 0.1 | 0 | | |
| S3 | 0.030 | 0.300 | 3 | 300 | | |
| S3 | 0.040 | 0.100 | 0.1 | 0 | | |

For Example 4 the dwell period takes place while the crimp head iris is fixed at 0.04 in, i.e., the final crimp diameter, followed by a further 25% diameter reduction for a brief period, followed by a return to the 0.04 in final diameter for an additional 3 second dwell. During the diameter reduction to 0.03 in the balloon pressure is 300 psi, and then the balloon pressure reduced when the iris is again moved from 0.03 in to 0.04 in.

Comparing the balloon pressure periods for Example 3 verses Example 4, in Example 3 balloon pressure is applied when the 0.04 in diameter is enforced by the crimp head, i.e., when the diameter is reduced (if any) from the unload diameter to the 0.04 in diameter. During the dwell period the stent is not loaded by the crimp head, nor is balloon pressure applied (a period of about 0.1 seconds). In Example 4, balloon pressure is applied when the diameter is reduced from 0.04 in to 0.03 in. Balloon pressure is relieved during the brief dwell period when the stent is allowed to expand up to about 0.04 in.

The cycles performed during Stage 3 according to Examples 3 and 4 are believed beneficial for the following reasons. First, by moving the stent diameter repeatedly from the unloaded or larger diameter, e.g., 0.04 as in Example 4, to the reduced diameter the material is worked to reduce recoil when the stent is finally removed from the crimper. Additionally, by moving between the two diameters while increasing and relieving pressure the balloon material can further nestle in between stent struts to increase the dislodgment force. Notably, it was found that the desired dislodgment force could be obtained by the cycling process adopted in Examples 3 and 4 without requiring a lengthy dwell time as in the prior art process, or be reducing the profile diameter beyond the desired amount. Thus, the desired dislodgment force could be obtained with a cycling process replacing the lengthy dwell period previously used to increase the dislodgment force, while maintaining the desired profile.

As mentioned earlier, the above mentioned processes, e.g., Example 3, are completed in substantially less time than previously thought possible. Prior to the invention, it was believed substantially more dwell time was needed for each stage to reduce recoil in the stent and permit pillowing to take effect. FIG. 1 shows a comparison of the time duration for a three stage process according to the invention, compared to the prior art three stage process. Plotted for each of the two processes are stent outer diameter (vertical bars) and temperature (line graph) verses time.

As can be appreciated from FIG. 1, the pre crimp processing time within the crimp head was reduced from about 70 seconds to about 25 second. The S2 or pillowing stage was reduced from about 180 seconds to 25 seconds. Finally, the S3 or final crimp/press stage was reduced from about 50 seconds to about 10 seconds. Thus, the overall process time for crimping the 3018 stent was reduced from about 350 seconds to about 60 seconds (not including leak test dwell period).

The processes of Examples 2, 3 and 4 each include maintaining pressure and temperature as the process transitions from S2 to S3, i.e., diameter reduction from the about 0.02 in diameter to 0.04 in or 0.03 in. Surprisingly, by maintaining pressure during this phase of the process there was a noticeable increase in the dislodgment force without any significant increase or change in profile diameter or deleterious effect on the stent deployment or balloon integrity. While not wishing to be tied to any particular theory, it is believed that the dislodgment or retention force increased by maintaining pressure during the S2 to S3 diameter reduction (as opposed to not applying balloon pressure as in Example 1) because the presence of balloon pressure helped to maintain the presence of balloon material between stent struts that was formed during S2. Without this balloon pressure being applied, it is believed that the about 25% to about 40% diameter reduction of the stent during the S2 to S3 transition had caused balloon material to be pushed or forced out from between stent struts as the spacing between the struts is reduced.

The examples given above refer to dimensions for a 3018 stent diameter and desired crimped profile for this stent. The principles expressed, however, are applicable to stents of different sizes. Accordingly, the disclosure should not be limited to a stent having a particular crimped profile or deployed diameter, such as the 3018 stent. Moreover, where there is recitation of "the stent", as opposed to "a stent", it would be incorrect to conclude that by use of the definite article "the" the discussion is necessarily referring to only the 3018 stent or only those stents having similar dimensions to that of the 3018 stent. One of ordinary skill will recognize that the principles discussed herein may be applied to stents other than the 3018 stent or similar stents.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method for crimping a stent to a balloon, comprising:
   i. elevating a temperature of the stent;
   ii. pre-crimping the stent including reducing a stent diameter to a first diameter while the stem is supported on a mandrel within a crimp head, wherein the stent has a first elevated temperature while the stent diameter is being reduced to the first diameter:
   iii. removing the stent and mandrel from the crimp head following the pre-crimping step and placing the stent on a balloon catheter to assemble a stent-catheter assembly, a balloon of the balloon catheter capable of being pressurized through a proximal end of an inflation lumen of the balloon catheter;
   iv. placing the stent-catheter assembly within the crimp head and increasing the stent temperature to a second elevated temperature, while the stent has the second elevated temperature, pressurizing the balloon via the inflation lumen while the stent-catheter assembly is within the crimp head, wherein the stent diameter expands to a second diameter that is up to about 25-30% greater than the first diameter when the balloon is pressurized;
   v. following step iv, pressing the stent into the balloon, the stent having a third elevated temperature, step v including reducing the stent diameter using the crimp head from the second diameter to about a final diameter while maintaining a balloon pressure including the step of reducing the stent diameter by about 25% to 40% from the second diameter while the balloon pressure is maintained; and
   vi. removing the stent-catheter assembly from the crimp head.

2. The method of claim 1, wherein step iii includes placing a sheath having an inner diameter of about 25% greater than the stent first diameter over the stent to protect a coating on the stent, wherein the sheath has a radial stiffness such that the presence of the sheath over the stent provides the up to about 25-30% greater than the first diameter restraint on stent expansion during step iv.

3. The method of claim 1 wherein the first diameter is about the same as the final diameter.

4. The method of claim 1 wherein the first, second and third elevated temperatures are the same.

5. The method of claim 1, wherein step v further includes steps (a) through (d):
   (a) maintaining the balloon pressure for a dwell period while the crimp head is at the final diameter:
   (b) after step (a). reducing the balloon pressure and withdrawing the crimp head from the stent to thereby allow the stent to recoil;
   (c) increasing the balloon pressure and moving the crimp head back to the final diameter following step (b); and
   (d) repeating steps (a) through (c) more than twice.

6. The method of claim 5, wherein the time duration in (b) is about 0.1 seconds, the balloon pressure for step (a) is about 300 psi and the balloon pressure is allowed to drop to a value attainable after 0.1 seconds before again increasing pressure and re-applying the crimp head to the stent according to step (c).

7. The method of claim 1, wherein step v further includes steps (a) through (e):
   (a) reducing the stent diameter to a third diameter. less than the final diameter while maintaining the balloon pressure;
   (b) maintaining the balloon pressure for a dwell period while the crimp head is at the third diameter;
   (c) after step (b), reducing the balloon pressure, followed by increasing a crimp head diameter to allow the stent to recoil from the third diameter to a larger diameter:
   (d) increasing the balloon pressure and moving the crimp head back to about the third diameter following step (c); and
   (e) repeating steps (b) through (d) than twice.

8. The method of claim 7, wherein the third diameter is between about 20-40% less than the final diameter.

9. The method of claim 8, wherein the time duration in (c) is about 0.1 seconds, the balloon pressure for step (a) is about 300 psi and the balloon pressure is allowed to drop to a value attainable after 0.1 seconds before again increasing pressure and re-applying the crimp head to the stent according to step (d).

10. A method for crimping a stent to a balloon, comprising:
    i. elevating a temperature of the stent;
    ii. pre-crimping the stent including reducing a stent diameter from a first diameter to a second diameter while the stent is supported on a mandrel within a crimp head, wherein the stent temperature has the elevated temperature while the diameter is being reduced to the second diameter;
    iii. removing the stent and mandrel from the crimp head following the pre-crimping step and placing the stent on a balloon catheter to assemble a stent-catheter assembly, a balloon of the balloon catheter capable of being pressurized through a proximal end of an inflation lumen of the balloon catheter;
    vi. placing a protective sheath over the stem, the protective sheath having a radial stiffness and an inner diameter that is about 20-30% greater than the stent outer diameter after step ii;
    v. placing the stent-catheter assembly within the crimp head and increasing the stent temperature to a second elevated temperature;
    vi. while the stent has the second elevated temperature, coupling the stent o the balloon including
       (a) pressurizing the balloon while the stent-catheter assembly is in the crimp head, wherein the balloon pressure is maintained at a pressure for a predetermined time period and the stent is restrained from expanding beyond about 20-30% of its diameter by the protective sheath,
       (b) following step (a), while maintaining the second elevated temperature and balloon pressure, reducing the diameter of the stent to a third diameter, less than the second diameter using the crimp head; and
    vii. removing the stent-catheter assembly from the crimp head.

11. The method of claim 10, step (b) further including the step of reducing the diameter of the stent to the third diameter while maintaining about the same balloon pressure as in step (a), followed by
    withdrawing the crimp head from the stent and reducing balloon pressure for about 0.1 seconds then again reducing the stent to the third diameter at the balloon pressure, and repeating this step a plurality of times to thereby cycle the stent with balloon material to increase a stent dislodgment force.

12. The method of claim 11 wherein step (b) further includes reducing the stent diameter down by about 40% simultaneously with the stent having the second elevated temperature and the balloon applying about a 300 psi pressure to a stent inner surface to thereby maintain a presence of balloon material between stent struts following step (a).

* * * * *